United States Patent
Hosokawa et al.

(10) Patent No.: US 11,744,781 B2
(45) Date of Patent: Sep. 5, 2023

(54) DENTAL PHOTOPOLYMERIZABLE COMPOSITION FOR 3D PRINTER

(71) Applicant: SHOFU INC., Kyoto (JP)

(72) Inventors: Mamoru Hosokawa, Kyoto (JP); Hidefumi Fujimura, Kyoto (JP)

(73) Assignee: SHOFU INC., Kyoto (JP)

( * ) Notice: Subject to any disclaimer, the term of this patent is extended or adjusted under 35 U.S.C. 154(b) by 23 days.

(21) Appl. No.: 17/001,853

(22) Filed: Aug. 25, 2020

(65) Prior Publication Data

US 2021/0137796 A1     May 13, 2021

(30) Foreign Application Priority Data

Aug. 26, 2019  (JP) ................. 2019-153828

(51) Int. Cl.
| | | |
|---|---|---|
| *A61K 6/887* | (2020.01) | |
| *B33Y 80/00* | (2015.01) | |
| *A61K 6/76* | (2020.01) | |
| *A61K 6/62* | (2020.01) | |
| *B33Y 70/10* | (2020.01) | |
| *A61K 6/17* | (2020.01) | |

(52) U.S. Cl.
CPC ............. *A61K 6/887* (2020.01); *A61K 6/17* (2020.01); *A61K 6/62* (2020.01); *A61K 6/76* (2020.01); *B33Y 70/10* (2020.01); *B33Y 80/00* (2014.12)

(58) Field of Classification Search
CPC .................................................. A61K 6/887
See application file for complete search history.

(56) References Cited

U.S. PATENT DOCUMENTS

| | | | |
|---|---|---|---|
| 5,849,459 A | 12/1998 | Hagiwara et al. | |
| 6,730,156 B1 * | 5/2004 | Windisch | A61K 6/20 |
| | | | 106/35 |
| 9,855,195 B2 * | 1/2018 | Takahashi | A61K 6/79 |
| 2016/0184189 A1 * | 6/2016 | Hagiwara | B29C 35/041 |
| | | | 522/174 |
| 2019/0254936 A1 | 8/2019 | Suzuki et al. | |
| 2020/0140614 A1 | 5/2020 | Parkar et al. | |

FOREIGN PATENT DOCUMENTS

| | | |
|---|---|---|
| EP | 3 363 424 | 8/2018 |
| JP | 8-224790 | 9/1996 |
| WO | 2015/126666 | 8/2015 |
| WO | 2018/0743 80 | 4/2018 |
| WO | 2019/023009 | 1/2019 |
| WO | WO-2019048963 A1 * 3/2019 ......... A61C 13/0004 |

OTHER PUBLICATIONS

Extended European Search Report dated Feb. 24, 2021 in corresponding European Patent Application No. 20192569.0.

* cited by examiner

*Primary Examiner* — Michael F Pepitone

(74) *Attorney, Agent, or Firm* — Wenderoth, Lind & Ponack, L.L.P.

(57) ABSTRACT

To provide a dental photopolymerizable composition which can prepare a dental restoration with excellent aesthetic and mechanical properties by optical three-dimensional modeling method (stereolithography). The dental photopolymerizable composition for 3D printer of the present invention comprises: a (a) (meth)acrylate-based polymerizable monomer consisting of a (a1) (meth)acrylate-based polymerizable monomer containing a urethane structure and a (a2) (meth)acrylate-based polymerizable monomer not containing a urethane structure, a (b) cohesive inorganic filler, and a (c) photopolymerization initiator, wherein; a ratio of the (a1) (meth)acrylate-based polymerizable monomer containing a urethane structure and the (a2) (meth)acrylate-based polymerizable monomer not containing a urethane structure in the (a) (meth)acrylate-based polymerizable monomer is 51 to 80: 49 to 20 pts.wt., a ratio of the (a) (meth)acrylate-based polymerizable monomer and the (b) cohesive inorganic filler is 50 to 91: 50 to 9 pts.wt., and the dental photopolymerizable composition for 3D printer contains 0.1 to 5 pts.wt. of the (c) photopolymerization initiator based on 100 pts.wt. of the (a) (meth)acrylate-based polymerizable monomer.

19 Claims, No Drawings

DENTAL PHOTOPOLYMERIZABLE COMPOSITION FOR 3D PRINTER

BACKGROUND OF THE INVENTION

Field of the Invention

The present invention relates to a photopolymerizable composition used for manufacturing a dental restoration with a 3D printer.

Description of the Related Art

Many proposals have been made for a method of preparing a three-dimensional modeled object by repeating a step of supplying light energy controlled in required amount to a liquid photo-curable resin and curing it in a thin film form, which is so-called optical three-dimensional modeling method (stereolithography), since the basic practical method was proposed.

The following is typical method for optically preparing a stereolithographic modeled object. The photopolymerizable composition in a container is cured in a prescribed thickness by selectively irradiating a computer controlled light so as to obtain a desired pattern. Then, a photopolymerizable composition is supplied on the upper surface of the lower surface of the cured layer to the thickness corresponding to one layer and is similarly irradiated with light to be cured. A commonly used method is to form a laminated body by repeating these steps until a three-dimensional modeled object having a final form has been prepared.

This method has recently been utilized in various industries because it can easily prepare a desired three-dimensional modeled object in a relatively short time even if the shape of the modeled object is complicated.

In particular, in the field of dental materials, since the shapes of prosthetic devices called inlay crown and bridge differ from clinical case to clinical case and are complicated, the application of stereolithography has been spread.

In the past, three-dimensional modeled objects prepared by stereolithography was mainly used for preparing prototypes. However, since the precision has been improved with technological development, the application has recently been expanded not only to prototypes but also to the preparation of final products. Therefore, not only modeling accuracy but also excellent strength characteristics has been required.

For the purpose of improving the strength, in general dental restorative materials, a method of blending inorganic filler has been used. However, when a photopolymerizable composition containing inorganic particles is used in stereolithography materials, since the inorganic particles scatter light, the scattered light causes excessive curing on the surface of the modeled object. As a result, there is a problem that the modeling accuracy is lowered and a modeled object with excellent aesthetic property cannot be obtained.

In this background, a resin composition for optical three-dimensional modeling containing an organic ultraviolet absorber is proposed as one example of a technique capable of optical three-dimensional modeling with excellent modeling accuracy in Japanese Unexamined Patent Application Publication No. H8-224790 A. However, Japanese Unexamined Patent Application Publication No. H8-224790 A does not specifically describe the utility of the resin composition for optical three-dimensional modeling in a composition in which it is essential to contain the inorganic particles, such as a dental material.

Further, a resin composition containing ultraviolet absorbing inorganic particles is proposed in International Publication No. WO201807438 A1.

However, although the feature of the resin composition for optical three-dimensional modeling described in International Publication No. WO201807438 A1 is the composition contains ultraviolet absorbing inorganic particles having an average primary particle diameter of 500 nm or less, the ultraviolet absorbing inorganic particles and the shapes of the inorganic particles contained as other component are not specifically described.

SUMMARY OF THE INVENTION

Technical Problem

An object of the present invention is to provide a dental photopolymerizable composition which can prepare a dental restoration with excellent aesthetic and mechanical properties by optical three-dimensional modeling method (stereolithography).

Solution to Problem

The present invention provides a dental photopolymerizable composition for 3D printer comprising: a (a) (meth)acrylate-based polymerizable monomer consisting of a (a1) (meth)acrylate-based polymerizable monomer containing a urethane structure and a (a2) (meth)acrylate-based polymerizable monomer not containing a urethane structure, a (b) cohesive inorganic filler, and a (c) photopolymerization initiator, wherein; a ratio of the (a1) (meth)acrylate-based polymerizable monomer containing a urethane structure and the (a2) (meth)acrylate-based polymerizable monomer not containing a urethane structure in the (a) (meth)acrylate-based polymerizable monomer is 51 to 80: 49 to 20 pts.wt., a ratio of the (a) (meth)acrylate-based polymerizable monomer and the (b) cohesive inorganic filler is 50 to 91: 50 to 9 pts.wt., and the dental photopolymerizable composition for 3D printer contains 0.1 to 5 pts.wt. of the (c) photopolymerization initiator based on 100 pts.wt. of the (a) (meth) acrylate-based polymerizable monomer.

In the dental photopolymerizable composition for 3D printer of the present invention, it is preferable that the (a) (meth)acrylate-based polymerizable monomer has a (a3) polyfunctional (meth) acrylate-based polymerizable monomer having a branched structure and at least 3 or more (meth)acrylate moieties.

In the dental photopolymerizable composition for 3D printer of the present invention, it is preferable that 1 to 15 wt. % of the (a) (meth)acrylate-based polymerizable monomer is the (a3) polyfunctional (meth) acrylate-based polymerizable monomer having a branched structure and at least 3 or more (meth)acrylate moieties.

In the dental photopolymerizable composition for 3D printer of the present invention, it is preferable that the (a3) polyfunctional (meth) acrylate-based polymerizable monomer having a branched structure and at least 3 or more (meth)acrylate moieties consists of the (a2) (meth)acrylate-based polymerizable monomer not containing a urethane structure.

In the dental photopolymerizable composition for 3D printer of the present invention, it is preferable that the (b) cohesive inorganic filler consists of 60 to 100 wt. % of $SiO_2$ and 0 to 40 wt. % of $ZrO_2$.

In the dental photopolymerizable composition for 3D printer of the present invention, it is preferable that the specific surface area of the (b) cohesive inorganic filler is 10 to 300 m²/g.

In the dental photopolymerizable composition for 3D printer of the present invention, it is preferable that the frequency average particle diameter of the (b) cohesive inorganic filler is within a range of 1 to 15 μm.

In the dental photopolymerizable composition for 3D printer of the present invention, it is preferable that the dental photopolymerizable composition for 3D printer further contains an additive.

In the dental photopolymerizable composition for 3D printer of the present invention, it is preferable that the additive contains one or more selected from a coloring material, an ultraviolet absorber, a polymerization inhibitor and a fluorescent agent.

In the dental photopolymerizable composition for 3D printer of the present invention, it is preferable that the dental photopolymerizable composition for 3D printer contains 0.0001 to 2 pts.wt. of the additive based on 100 pts.wt. of the dental photopolymerizable composition for 3D printer excluding the additive.

The present invention also provides a dental restoration prepared by a stereolithography-type 3D printer by using the dental photopolymerizable composition for 3D printer of the present invention.

Advantageous Effects of Invention

The photopolymerizable composition of the present invention can prepare a modeled object with excellent aesthetic property and strength characteristic when it is modeled by optical three-dimensional modeling (stereolithography). Therefore, the photopolymerizable composition of the present invention can be suitably used as a dental material (for example, a dental prosthesis device).

DETAILED DESCRIPTION OF THE PREFERRED EMBODIMENTS

The present invention will be described in detail below.

The dental photopolymerizable composition for 3D printer of the present invention comprises: a (a) (meth)acrylate-based polymerizable monomer consisting of a (a1) (meth)acrylate-based polymerizable monomer containing a urethane structure and a (a2) (meth)acrylate-based polymerizable monomer not containing a urethane structure, a (b) cohesive inorganic filler, and a (c) photopolymerization initiator, wherein; a ratio of the (a1) (meth)acrylate-based polymerizable monomer containing a urethane structure and the (a2) (meth)acrylate-based polymerizable monomer not containing a urethane structure in the (a) (meth)acrylate-based polymerizable monomer is 51 to 80: 49 to 20 pts.wt., a ratio of the (a) (meth)acrylate-based polymerizable monomer and the (b) cohesive inorganic filler is 50 to 91: 50 to 9 pts.wt., and the dental photopolymerizable composition for 3D printer contains 0.1 to 5 pts.wt. of the (c) photopolymerization initiator based on 100 pts.wt. of the (a) (meth) acrylate-based polymerizable monomer.

The (a) (meth)acrylate-based polymerizable monomer consists of the (a1) (meth)acrylate-based polymerizable monomer containing a urethane structure and the (a2) (meth) acrylate-based polymerizable monomer not containing a urethane structure. In the present specification, "urethane structure" means a structure "—NH—CO—O—". By containing a larger amount of the (meth)acrylate containing a urethane structure than the (meth)acrylate not containing a urethane structure, the interaction with the inorganic filler becomes good, it is possible to maintain the appearance of the surface of the modeled object in good. Further, it is possible to impart toughness to the strength characteristics of the modeled object.

Therefore, the (a1) (meth)acrylate-based polymerizable monomer containing a urethane structure is contained within a range of 51 to 80 pts.wt., preferably 51 to 75 pts.wt., further preferably 51 to 70 pts.wt., in the (a) (meth)acrylate-based polymerizable monomer. In addition, the (a2) (meth) acrylate-based polymerizable monomer not containing a urethane structure is contained within a range of 20 to 49 pts.wt., preferably 25 to 49 pts.wt., further preferably 30 to 49 pts.wt., in the (a) (meth)acrylate-based polymerizable monomer. When the (a1) (meth)acrylate-based polymerizable monomer containing a urethane structure is contained in an amount of more than 80 pts.wt. in the (a) (meth) acrylate-based polymerizable monomer, there is a problem that the modeled object becomes soft.

It is preferable that (a) (meth)acrylate-based polymerizable monomer contains the (a3) polyfunctional (meth) acrylate-based polymerizable monomer having a branched structure and at least 3 or more (meth)acrylate moieties. This component accelerates curing of the surface of the modeled object. Therefore, a smooth surface can be easily obtained, and a good appearance can be maintained.

The (a3) polyfunctional (meth) acrylate-based polymerizable monomer having a branched structure and at least 3 or more (meth)acrylate moieties is contained within a range of 1 to 15 pts.wt., preferably 1 to 10 pts.wt., further preferably 3 to 7 pts.wt., in the (a) (meth)acrylate-based polymerizable monomer. When the (a3) polyfunctional (meth) acrylate-based polymerizable monomer having a branched structure and at least 3 or more (meth)acrylate moieties is contained in an amount of more than 15 pts.wt. in the (a) (meth)acrylate-based polymerizable monomer, there may be a problem that the modeled object becomes hard and brittle.

The (a3) polyfunctional (meth) acrylate-based polymerizable monomer having a branched structure and at least 3 or more (meth)acrylate moieties has preferably 3 to 10 (meth)acrylate moieties, more preferably 4 to 9 (meth) acrylate moieties, and further preferably 5 to 7 (meth) acrylate moieties.

Examples of the (a1) (meth)acrylate-based polymerizable monomer containing a urethane structure include, but are not limited thereto, urethane di(meth)acrylate obtained by reacting aliphatic diisocyanate compound such as hexamethylene diisocyanate, 2,2,4-trimethyl hexamethylene diisocyanate, isophorone diisocyanate and hydrogenated diphenylmethane diisocyanate or organic diisocyanate compound such as diphenylmethane diisocyanate and toluene diisocyanate with polymerizable monomer having hydroxyl group such as hydroxyethyl (meth)acrylate, hydroxypropyl (meth) acrylate, hydroxybutyl (meth)acrylate and hydroxypentyl (meth)acrylate and the like.

For example, 7,7,9-trimethyl-4,13-dioxo-3,14-dioxa-5, 12-diaza hexadecane-1,16-diyl dimethacrylate (UDMA) synthesized by urethane reaction of 2,2,4-trimethyl hexamethylene diisocyanate with 2-hydroxyethyl methacrylate (HEMA), radical polymerizable monomers synthesized by the urethane reaction of HEMA or hydroxyethyl acrylate (HEA) with 2,4-toluylene diisocyanate, hydride diphenylmethane diisocyanate, naphthalene diisocyanate or hexamethylene diisocyanate, respectively urethane diacrylates obtained by the reaction of aliphatic and/or aromatic diisocyanates with glycerol (meth) aclylate or 3-methacryl-2-hydroxypropyl ester, and a urethane reaction product of 1,3-bis (2-isocyanate-2-propyl) benzene and a compound having a hydroxy group, and the like.

Specific examples include 2,2,4-trimethyl hexamethylene bis (2-carbamoyloxyethyl) dimethacrylate, 2,7,7,9,15-pentamethyl-4,13-dioxo-3,14-dioxa-5,12-diaza hexadecane-1,16-diyldiacrylate, 2,7,7,9,15-pentamethyl-4,13,18-trioxo-3,14,17-trioxa-5,12-diazaicos-19-enylmethacrylate, 2,8,10,10,15-penta methyl-4,13,18-trioxo-3,14,17-trioxa-5,12-diazaicos-19-enylmethacrylate, 2,7,7,9,15-pentamethyl-4,13-dioxo-3,14-dioxa-5,12-diaza hexadecane-1,16-diylbis (2-methylacrylate), 2,2'-(cyclohexane-1,2-diylbis (methylene)) bis (azandiyl) bis (oxomethylene) bis (oxy) bis (propane-2,1-diyl) diacrylate, 2-((2-(((1-(acryloyloxy) propan-2-yloxy) carbonylamino) methyl) cyclohexyl) methylcarbamoyloxy) propylmethacrylate, 2,2'-(cyclohexane-1,2-diylbis (methylene)) bis (azandiyl) bis (oxomethylene) bis (oxy) bis (propane-2,1-diyl) bis (2-methylacrylate), 2,2'-(bicyclo [4.1.0] heptane-3,4-diylbis (methylene)) bis (azandiyl) bis (oxomethylene) bis (oxy) bis (propane-2,1-diyl) diacrylate, 2-((4-(((1-(acryloyloxy) propan-2-yloxy) carbonylamino) methyl) bicyclo [4.1.0] heptane-3-yl) methylcarbamoyloxy) propyl methacrylate, 2,2'-(bicyclo [4.1.0] heptane-3,4-diyl bis (methylene)) bis (azandiyl) bis (oxomethylene) bis (oxy) bis (propane-2,1-diyl) bis (2-methylacrylate), 7,7,9-trimethyl-4,13-dioxo-3,14-dioxa-5,12-diaza hexadecane-1,16-diyldiacrylate, 7,7,9-trimethyl-4,13,18-trioxo-3,14,17-trioxa-5,12-diazaicos-19-enyl methacrylate, 8,10,10-trimethyl-4,13,18-trioxo-3,14,17-trioxa-5,12-diazaicos-19-enyl methacrylate, 7,7,9-trimethyl-4,13-dioxo-3,14-dioxa-5,12-diaza hexadecane-1,16-diylbis (2-methylacrylate), 4,13-dioxo-3,14-dioxa-5,12-diaza hexadecane-1,16-diyldiacrylate, 4,13,18-trioxo-3,14,17-trioxa-5,12-diazaicos-19-enyl methacrylate, 4,13-dioxo-3,14-dioxa-5,12-diaza hexadecane-1,16-diyl bis (2-methylacrylate), 2-(1-(2-((2-(acryloyloxy) ethoxy) carbonylamino)-4,4-dimethylcyclohexyl) ethylcarbamoyloxy) ethylmethacrylate, 2-(1-(2-((2-(acryloyloxy) ethoxy) carbonylamino) ethyl)-5,5-dimethyl cyclohexyl carbamoyloxy) ethyl methacrylate, 2-(2-(((1-(methacryloyloxy) propan-2-yloxy) carbonylamino) methyl)-2,5,5-trimethyl cyclohexyl carbamoyloxy) propane-1,3-diylbis (2-methyl) acrylate, 2-(2-(((1-(methacryloyloxy) propane-2-yloxy) carbonylamino) methyl)-2,5,5-trimethyl cyclohexyl carbamoyloxy) propane-1,3-diyldiacrylate, 2-(2-(((1-(acryloyloxy) propan-2-yloxy) carbonylamino) methyl)-2,5,5-trimethyl cyclohexyl carbamoyloxy) propane-1,3-diylbis (2-methylacrylate), 3-(15-(2-(acryloyloxy) ethyl)-3,12,19-trioxo-2,13,18-trioxa-4,11-diazahenicos-20-enyl) pentane-1,5-diyldiacrylate, ethyl)-3,12,19-trioxo-2,13,18-trioxa-4,11-diazahenicos-20-enyl) pentane-1,5-diyl bis (2-methyl acrylate), 2,2'-(cycrohexane-1,2-diyl bis (methylene)) bis (azandiyl) bis (oxomethylene) bis (oxy) bis (ethane-2,1-diyl) diacrylate, 2-((2-(((2-(acryloyloxy) ethoxy) carbonylamino) methyl) cyclohexyl) methyl carbamoyloxy) ethyl methacrylate, 2,2'-(cycryhexane-1,2-diyl bis (methylene)) bis (azandiyl) bis (oxomethylene) bis (oxy) bis (ethane-2,1-diyl) bis (2-methylacrylate), 2,15-bis (cyclohexyl oxymethyl)-4,13-dioxo-3,14-dioxa-5,12-diazahexadecane-1,16-diyldiacrylate, 2,15-bis (cyclohexyloxymethyl)-4,13-dioxo-3,14-dioxa-5,12-diazahexadecane-1,16-diyl bis (2-methylacrylate), 2,15-bis (cyclohexyloxymethyl)-4,13,18-trioxo-3,14,17-trioxa-5,12-diazaicos-19-enylmethacrylate, 1,18-bis (cyclohexyloxy)-5,14-dioxo-4,15-dioxa-6,13-diaza octadecane-2,17-diyldiacrylate, 1-(cyclohexyloxy)-17-(cyclohexyloxymethyl)-5,14,19-trioxo-4,15,18-trioxa-6,13-diaza henicos-20-en-2-yl methacrylate, 1,18-bis (cyclohexyloxy)-5,14-dioxo-4,15-dioxa-6,13-diaza octadecane-2,17-diyl bis (2-methylacrylate), 7,7,9-trimethyl-4,13-dioxo-3,14-dioxa-5,12-diaza hexadecane-1,16-diyl bis (2-methylacrylate), 7,7,9-trimethyl-4,13-dioxo-3,14-dioxa-5,12-diaza hexadecane-1,16-diyldiacrylate, 2,2'-(1,3-phenylene bis (methylene)) bis (azandiyl) bis (oxomethylene) bis (oxy) bis (ethane-2,1-diyl) bis (2-methacrylate), 2,2'-(1,3-phenylene bis (methylene)) bis (azandiyl) bis (oxomethylene) bis (oxy) bis (ethane-2,1-diyl) diacrylate, 2-(3-(((2-(acryloyloxy) ethoxy) carbonylamino) methyl) benzyl carbamoyloxy) ethyl methacrylate, 2,2'-(1,3-phenylene bis (methylene)) bis (methyl azandiyl) bis (oxomethylene) bis (oxy) bis (ethane-2,1-diyl) bis (2-methacrylate), 2,2'-(1,3-phenylene bis (methylene)) bis (methyl azandiyl) bis (oxomethylene) bis (oxy) bis (ethane-2,1-diyl) diacrylate, 2-((3-((((2-(acryloyloxy) ethoxy) carbonyl) (methyl) amino) methyl) benzyl) (methyl) carbamoyloxy) ethyl methacrylate, 2,2'-(1,3-phenylene bis (methylene)) bis (azandiyl) bis (oxomethylene) bis (oxy) bis (propane-2,1-diyl) bis (2-methylacrylate), 2,2'-(1,3-phenylene bis (methylene)) bis (azandiyl) bis (oxomethylene) bis (oxy) bis (propane-2,1-diyl) diacrylate, 2-(3-(((2-(acryloyloxy) ethoxy) carbonylamino) methyl) benzyl carbamoyloxy) propyl methacrylate, 2-(3-(((1-(acryloyloxy) propan-2-yloxy) carbonylamino) methyl) benzyl carbamoyloxy) ethyl methacrylate, 4,4'-(1,3-phenylene bis (methylene)) bis (azandiyl) bis oxomethylene) bis (oxy) bis (4,1-phenylene) bis (2-methylacrylate), 4,4'-(1,3-phenylene bis (methylene)) bis (azandiyl) bis oxomethylene bis (oxy) bis (4,1-phenylene) diacrylate, 4-(3-(((4-(acryloxy) phenoxy) carbonylamino) methyl) benzyl carbamoyloxy) phenyl methacrylate, 4,4'-(1,3-phenylene bis (methylene)) bis (azandiyl) bis (oxomethylene) bis (oxy) bis (butane-4,1-diyl) bis (2-methylacrylate), 4,4'-(1,3-phenylene bis (methylene)) bis (azandiyl) bis (oxomethylene) bis (oxy) bis (butane-4,1-diyl) diacrylate, 4-(3-(((4-(acryloyloxy) butoxy) carbonylamino) methyl) benzyl carbamoyloxy) butyl methacrylate, 2,2'-(1,3-phenylene bis (methylene)) bis (azandiyl) bis (oxomethylene) bis (oxy) bis (3-phenoxypropane-2,1-diyl) bis (2-methylacrylate), 4-(3-(((4-(acryloyloxy) butoxy) carbonylamino) methyl) benzyl carbamoyloxy) butyl methacrylate, 2,2'-(1,3-phenylene bis (methylene)) bis (azandiyl) bis (oxomethylene) bis (oxy) bis (3-phenoxypropane-2,1-diyl) bis (2-methylacrylate), 2,2'-(1, 3-phenylene bis (methylene)) bis (azandiyl) bis (oxomethylene) bis (oxy) bis (3-phenoxypropane-2,1-diyl) diacrylate, 2-(3-(((1-(acryloyloxy)-3-phenoxypropan-2-yloxy) carbonylamino) methyl) benzyl carbamoyloxy)-3-phenoxypropyl methacrylate, 2-2'-(1,3-phenylene bis (methylene)) bis (azandiyl) bis (oxomethylene) bis (oxy) bis (3-(phenylamino) propan-2,1-diyl) bis (2-methyl) acrylate, 2-2'-(1, 3-phenylene bis (methylene)) bis (azandyl) bis (oxomethylene) bis (oxy) bis (3-(phenylamino) propan-2,1-diyl) diacrylate, 2-(3-(((1-(acryloyloxy)-3-(phenylamino) propan-2-yloxy) carbonylamino) methyl) benzyl carbamoyloxy)-3-(phenylamino) propyl methacrylate, 2,2'-(1,3-phenylene bis (methylene)) bis (azandiyl) bis (oxomethylene) bis (oxy) bis (3-(phenylthio) propan-2,1-diyl) bis (2-methylacrylate), 2,2'-(1,3 phenylene bis (methylene)) bis (azandiyl) bis (oxomethylene) bis (oxy) bis (3-(phenylthio) propan-2,1-diyl) diacrylate, 2-(3-(((1-(acryloxy)-3-(phenylthio) propan-2-yloxy) carbonylamino) methyl) benzyl carbamoyloxy)-3-(phenylthio) propyl methacrylate, 2,2'-(1,3-phenylene bis (methylene)) bis (azandyl) bis (oxomethylene) bis (oxy) bis (3-(benzyloxy) propan-2,1-diyl) bis (2-methyl) acrylate, 2,2'-(1,3-phenylene bis (methylene)) bis (azandyl) bis (oxomethylene) bis (oxy) bis (3-

(benzyloxy) propan-2,1-diyl) diacrylate, 2-(3-(((1-(acryloyloxy)-3-(benzyloxy) propan-2-yloxy) carbonylamino) methyl) benzyl carbamoyloxy)-3-(benzyloxy) propyl methacrylate, 2,2'-(1,3-phenylene bis (methylene)) bis (azandiyl) bis (oxomethylene) bis (oxy) bis (3-(methacryloyloxy) propan-2,1-diyl) dibenzoate, 2,2'-(1,3-phenylene bis (methylene)) bis (azandiyl) bis (oxomethylene) bis (oxy) bis (3-(acryloyloxy) propan-2,1-diyl) dibenzoate, 2,2'-(1,3-phenylene bis (methylene)) bis (azandiyl) bis (oxomethylene) bis (oxy) bis (3-(2-phenylacetoxy) propan-2,1-diyl) bis (2-methylacrylate), 2,2'-(1,3-phenylene bis (methylene)) bis (azandiyl) bis (oxomethylene) bis (oxy) bis (3-(2-phenylacetoxy) propan-2,1-diyl) diacrylate, 2-(3-(((1-(acryloyloxy)-3-(2-phenylacetoxy) propan-2-yloxy) carbonylamino) methyl) benzyl carbamoyloxy)-3-(2-phenylacetoxy) propyl methacrylate, 2,2'-(2,2'-(1,3-phenylene) bis (propane-2,2-diyl)) bis (azandiyl) bis (oxomethylene) bis (oxy) bis (ethane-2,1-diyl) bis (2-methacrylate), 2,2'-(2,2'-(1,3-phenylene) bis (propane-2,2-diyl)) bis (azandiyl) bis (oxomethylene) bis (oxy) bis (ethane-2,1-diyl) diacrylate, 2-(2-(3-(2-((2-(acryloyloxy) ethoxy) carbonylamino) propan-2-yl) phenyl) propan-2-yl carbamoyloxy) ethyl methacrylate, 2,2'-(2,2'-(1,3-phenylene) bis (propane-2,2-diyl)) bis (methylazandiyl) bis (oxomethylene) bis (oxy) bis (ethane-2,1-diyl) bis (2-methacrylate), 2,2'-(2,2'-(1,3-phenylene) bis (propane-2,2-diyl)) bis (methylazandiyl) bis (oxomethylene) bis (oxy) bis (ethane-2,1-diyl) diacrylate, 2-((2-(3-(2-(((2-(acryloyloxy) ethoxy) carbonyl) (methyl) amino) propan-2-yl) phenyl) propan-2-yl) (methyl) carbamoyloxy) ethyl methacrylate, 2,2'-(2,2'-(1,3-phenylene) bis (propane-2,2-diyl)) bis (azandiyl) bis (oxomethylene) bis (oxy) bis (propane-2,1-) diyl bis (2-methylacrylate), 2,2'-(2,2'-(1,3-phenylene) bis (propane-2,2-diyl)) bis (azandiyl) bis (oxomethylene) bis (oxy) bis (propane-2,1-diyl) diacrylate, 2-(2-(3-(2-((2-(acryloyloxy) ethoxy) carbonylamino) propan-2-yl) phenyl) propan-2-yl carbamoyloxy) propyl methacrylate, 2-(2-(3-(2-(1-(acryloyloxy) propane-2-yloxy) carbonylamino) propane-2-yl) carbamoyloxy) ethyl methacrylate, 4,4'-(2,2'-(1,3-phenylene) bis (propane-2,2-diyl)) bis (azandiyl) bis (oxomethylene) bis (oxy) bis (4,1-phenylene) bis (2-methylacrylate), 4,4'-(2,2'-(1,3-phenylene) bis (propane-2,2-diyl)) bis (azandiyl) bis (oxomethylene) bis (oxy) bis (4,1-phenylene) diacrylate, 4-(2-(3-(2-((4-(acryloyloxy) phenoxy) carbonylamino) propan-2-yl) phenyl) propan-2-ylcarbamoyloxy) phenyl methacrylate, 4,4'-(2,2'-(1,3-phenylene) bis (propane-2,2-diyl)) bis (azandiyl) bis (oxomethylene) bis (oxy) bis (butane-4,1-diyl) bis (2-methacrylate), 4,4'-(2,2'-(1,3-phenylene) bis (propane-2,2-diyl)) bis (azandiyl) bis (oxomethylene) bis (oxy) bis (butane-4,1-diyl) diacrylate, 4-(2-(3-(2-((4-(acryloyloxy) butoxy) carbonylamino) propan-2-yl) phenyl) propan-2-ylcarbamoyloxy) butyl methacrylate, 2,2'-(2,2'-(1,3-phenylene) bis (propane-2,2-diyl)) bis (azandiyl) bis (oxomethylene) bis (oxy) bis (3-phenoxypropane-2,1-diyl) bis (2-methacrylate), 2,2'-(2,2'-(1,3-phenylene) bis (propane-2,2-diyl)) bis (azandiyl) bis (oxomethylene) bis (oxy) bis (3-phenoxypropane-2,1-diyl) diacrylate, 2-(2-(3-(2-((1-(acryloyloxy)-3-phenoxypropan-2-yloxy) carbonylamino) propan-2-yl) phenyl) propan-2-ylcarbamoylxi)-3-phenoxypropyl methacrylate, 2,2'-(2,2'-(1,3-phenylene) bis (propane-2,2-diyl)) bis (azandiyl) bis (oxomethylene) bis (oxy) bis (3-(phenylamino) propane-2,1-diyl) bis (2-methacrylate), 2,2'-(2,2'-(1,3-phenylene) bis (propane-2,2-diyl)) bis (azandiyl) bis (oxomethylene) bis (oxy) bis (3-(phenylamino) propane-2,1-diyl) diacrylate, 2-(2-(3-(2-((1-(acryloyloxy)-3-(phenylamino) propan-2-yloxy) carbonylamino) propan-2-yl) phenyl) propan-2-ylcarbamoyloxy)-3-(phenylamino) propyl methacrylate, 2,2'-(2,2'-(1,3-phenylene) bis (propane-2,2-diyl)) bis (azandiyl) bis (oxomethylene) bis (oxy) bis (3-(phenylthio) propane-2,1-diyl) bis (2-methylacrylate), 2,2'-(2,2'-(1,3-phenylene) bis (propane-2,2-diyl)) bis (azandiyl) bis (oxomethylene) bis (oxy) bis (3-(phenylthio) propane-2,1-diyl) diacrylate, 2-(2-(3-(2-((1-(acryloyloxy)-3-(phenylthio) propan-2-yloxy) carbonylamino) propan-2-yl) phenyl) propan-2-ylcarbamoyloxy)-3-(phenylthio) propyl methacrylate, 2-2'-(2,2'-(1,3-phenylene) bis (propane-2,2-diyl)) bis (azandiyl) bis (oxomethylene) bis (3-(benzyloxy) propane-2,1-diyl) bis (2-methylacrylate), 2-2'-(2,2'-(1,3-phenylene) bis (propane-2,2-diyl)) bis (azandiyl) bis (oxomethylene) bis (3-(benzyloxy) propane-2,1-diyl) diacrylate, 2-(2-(3-(2-((1-(acryloyloxy)-3-(benzyloxy) propan-2-yloxy) carbonylamino) propan-2-yl) phenyl) propan-2-ylcarbamoyloxy)-3-(benzyloxy) propyl methacrylate, 2,2'-(2,2'-(1,3-phenylene) bis (propane-2,2-diyl)) bis (azandiyl) bis (oxomethylene) bis (oxy) bis (3-(methacryloyloxy) propane-2,1-diyl) dibenzoate, 2,2'-(2,2'-(1,3-phenylene) bis (propane-2,2-diyl)) bis (azandiyl) bis (oxomethylene) bis (oxy) bis (3-(acryloyloxy) propane-2,1-diyl) dibenzoate, 2,2'-(2,2'-(1,3-phenylene) bis (propane-2,2-diyl)) bis (azandiyl) bis (oxomethylene) bis (oxy) bis (3-(2-phenyl acetoxy) propane-2,1-diyl) bis (2-methacrylate), 2,2'-(2,2'-(1,3-phenylene) bis (propane-2,2-diyl)) bis (azandiyl) bis (oxomethylene) bis (oxy) bis (3-(2-phenylacetoxy) propane-2,1-diyl) diacrylate, 2-(2-(3-(2-((1-(acryloyloxy)-3-(2-phenylacetoxy) propan2-yloxy) carbonylamino) propan-2-yl) phenyl) propan-2-ylcarbamoyloxy)-3-(2-phenylacetoxy) propyl methacrylate.

Among them, as shown in chemical formula, a composition containing a radical polymerizable monomer having a benzene ring and/or a cyclohexane ring and a urethane bond in the molecular skeleton, such as ((((propane-2,2-diyl bis (4,1-phenylene)) bis (azanediyl)) bis (carbonyl)) bis (oxy)) bis (ethane-2,1-diyl) bis (2-methylacrylate), ((((methylene bis (4,1-phenylene)) bis (azanediyl)) bis (carbonyl)) bis (oxy)) bis (ethane-2,1-diyl) bis (2-methylacrylate), ((((2-methyl-1,3-phenylene) bis (azanediyl)) bis (carbonyl)) bis (oxy)) bis (ethane-2,1-diyl) bis (2-methylacrylate), ((((cyclohexane-1,3-diylbis (methylene)) bis (azanediyl)) bis (carbonyl)) bis (oxy)) bis (ethane-2,1-diyl) diacrylate, ((((methylene bis (4,1-phenylene)) bis (azanediyl)) bis (carbonyl)) bis (oxy)) bis (ethane-2, 1-diyl) diacrylate, (((((2-methyl-1, 3-phenylene) bis (azanediyl)) bis (carbonyl)) bis (oxy)) bis (ethane-2,1-diyl) diacrylate, (((((cyclohexane-1,3-diylbis (methylene)) bis (azanediyl)) bis (carbonyl)) bis (oxy)) bis (ethane-2,1-diyl) bis (2-methylacrylate), and the like.

[Chemical Formula 1]
[Chemical Formula 2]

Among these, 2,2,4-trimethyl hexamethylene bis (2-carbamoyloxyethyl) dimethacrylate and 2,7,7,9,15-pentamethyl-4,13-dioxo-3,14-dioxa-5,12-diazahexadecane-1,16-diyldiacrylate are preferred, and 2,2,4-trimethyl hexamethylene bis (2-carbamoyloxyethyl) dimethacrylate is particularly preferred.

These can be used singly or in combinations of a plurality thereof.

Examples of the (a2) (meth)acrylate-based polymerizable monomer not containing a urethane structure include 2-hydroxyethyl (meth)acrylate, 2-hydroxypropyl (meth)acrylate, 3-hydroxypropyl (meth)acrylate, 4-hydroxybutyl (meth) acrylate, 6-hydroxyhexyl (meth) acrylate, 10-hydroxydecyl (meth) acrylate, propylene glycol mono (meth) acrylate, glycerol mono (meth) acrylate, erythritol mono (meth) acrylate, methyl (meth) acrylate, ethyl (meth) acrylate, propyl (meth)acrylate, isopropyl(meth)acrylate, n-butyl(meth)acrylate, sec-butyl(meth)acrylate, t-butyl(meth)acrylate, isobutyl(meth)acrylate, n-hexyl(meth) acrylate, cyclohexyl (meth)acrylate, lauryl (meth)acrylate, cetyl (meth)acrylate, stearyl (meth)acrylate, isobornyl (meth)acrylate, benzyl (meth)acrylate, phenyl (meth)acrylate, 2,3-dibromopropyl (meth)acrylate,3-(meth)acryloyloxypropyltrimethoxysilane, 11-(meth)acryloyloxyundecyltrimethoxysilane, (meth)acrylamide, ethylene glycol dimethacrylate, diethylene glycol dimethacrylate, triethylene glycol dimethacrylate, polyethylene glycol dimethacrylate, 2,2-bis[4-(methacryloxyethoxy)phenyl]propane, tricyclodecanedimethanol dimethacrylate, 1,10-decanediol dimethacrylate, 1,6-hexanediol dimethacrylate, 1, 9-nonanediol dimethacrylate, neopentyl glycol dimethacrylate, 2-hydroxy-1,3-dimethacryloxypropane and the like.

These can be used singly or in combinations of a plurality thereof. Among them, triethylene glycol dimethacrylate and 2,2-bis (4-methacryloxy polyethoxyphenyl) propane are preferable, and 2,2-bis (4-methacryloxy polyethoxyphenyl) propane is particularly preferable.

These may be used alone or in combination of two or more.

The (a3) polyfunctional (meth) acrylate-based polymerizable monomer having a branched structure and at least 3 or more (meth)acrylate moieties is preferably (meth)acrylate-based polymerizable monomer not containing a urethane structure. Specific examples include trimethylolpropane trimethacrylate, ethoxylated trimethylolpropane trimethacrylate, ditrimethylolpropane tetramethacrylate, tris (2-hydroxyethyl) isocyanurate trimethacrylate, dipentaerythritol pentamethacrylate, ethoxylated pentaerythritol tetramethacrylate, propoxylated glyceryl trimethacrylate, propoxylated trimethylolpropane trimethacrylate, pentaerythritol triacrylate, trimethylolpropane triacrylate, ditrimethylolpropane tetraacrylate, ethoxylated pentaerythritol tetraacrylate, pentaerythritol tetraacrylate, dipentaerythritol pentaacrylate, dipenta erythritol polyacrylate, dipentaerythritol hexaacrylate and the like. Among these, dipentaerythritol hexaacrylate, ditrimethylolpropane tetraacrylate and pentaerythritol triacrylate are preferable. These may be used alone or in combination of two or more.

In the (b) cohesive inorganic filler, nano-sized primary particles are aggregated to form secondary particles. The (b) cohesive inorganic filler preferably has spherical shape. In addition, the (b) cohesive inorganic filler preferably consists of $SiO_2$ and $ZrO_2$.

The (b) cohesive inorganic filler is preferably a cohesive inorganic filler containing 60 to 100 wt. % of $SiO_2$ and 0 to 40 wt. % of $ZrO_2$, more preferably 70 to 90 wt. % of $SiO_2$ and 10 to 30 wt. % of $ZrO_2$, further preferably 75-85 wt. % of $SiO_2$ and 15 to 25 wt. % of $ZrO_2$. Further, the (b) cohesive inorganic filler is preferably a cohesive inorganic filler consisting of 60 to 100 wt. % of $SiO_2$ and 0 to 40 wt. % of $ZrO_2$, more preferably 70 to 90 wt. % of $SiO_2$ and 10 to 30 wt. % of $ZrO_2$, further preferably 75-85 wt. % of $SiO_2$ and 15 to 25 wt. % of $ZrO_2$.

Further, the primary particles forming the secondary particles may contain a small amount of other components.

By using these cohesive inorganic fillers, it is possible to obtain a dental restoration with excellent transparency and high aesthetic property.

The specific surface area of the (b) cohesive inorganic filler is preferably 10 to 300 $m^2/g$, more preferably 10 to 250 $m^2/g$, and further preferably 15 to 200 $m^2/g$.

When the specific surface area is too high, the viscosity of the dental photopolymerizable composition for 3D printer will be too high and it tends to be difficult to obtain a good modeled object. When the specific surface area is too low, sedimentation tends to occur easily in the composition.

The frequency average particle diameter of the (b) cohesive inorganic filler, that is, of the secondary particles is preferably within a range of 1 to 15 μm, more preferably 1 to 10 μm, and further preferably 2 to 5 μm. When the particle diameter is less than 1 μm, light scattering by the inorganic particles tends to be small. However the viscosity of the photopolymerizable composition tends to be high, therefore there is a case that the effect of improving the modelability may not be obtained. When the particle size is more than 15 μm, because the particle size is large, there is a case that it may be difficult to obtain a dental restoration with excellent aesthetic property.

In the present specification, the frequency average particle diameter means 50% diameter, and can be measured by, for example, a laser diffraction type particle size measuring machine.

The frequency average particle size of the primary particles constituting the aggregated particles is preferably within a range of 5 to 50 nm, more preferably 8 to 40 nm.

The cohesive inorganic filler is preferably surface-treated with a silane coupling agent.

Specific examples of silane coupling agents include methyl trimethoxysilane, dimethyl dimethoxysilane, phenyl trimethoxysilane, diphenyl dimethoxysilane, methyl triethoxysilane, dimethyl diethoxysilane, vinyl trimethoxysilane, vinyl triethoxysilane, methyl dichlorosilane, dimethyl dichlorosilane, trimethyl chlorosilane, vinyl trichlorosilane, trimethyl bromosilane, diethylsilane and the like.

The cohesive inorganic filler is preferably surface-treated with 2 to 30 pts.wt. of the silane coupling agent based on the cohesive inorganic filler by a predetermined method.

In the present invention, other filler other than the cohesive inorganic filler, for example, an inorganic filler may be contained, and when the other filler other than the cohesive inorganic filler is contained, the content thereof may be preferably 10 pts.wt. or less. In the present invention, it is also possible to contain no other filler other than the cohesive inorganic filler.

In the present invention, the ratio of the (a) (meth) acrylate-based polymerizable monomer and the (b) cohesive inorganic filler is 50 to 91: 50 to 9 pts.wt., preferably 65 to 90: 35 to 10 pts.wt., further preferably 70 to 87: 30 to 13 pts.wt. When the ratio of the (B) cohesive inorganic filler exceeds 50, there is a case that the viscosity of the composition may become too high. When the ratio of the (B) cohesive inorganic fille is less than 10, there is a case that the improvement of characteristics such as bending strength by the cohesive inorganic filler may be insufficient.

Examples of the (C) photopolymerization initiator include benzophenones, α-diketones, compounds, acylphosphine oxides such as (bis) acylphosphine oxides and water-soluble acylphosphine oxides, thioxanthones, quaternary ammonium salt of thioxanthones, ketals, coumarins, anthraquinones, benzoins such as benzoin alkyl ether and α-aminoketone compounds.

Specific examples of benzophenones used as photopolymerization initiators include benzophenone, 4,4'-bis (dimethylamino) benzophenone, 2-carbomethoxy benzophenone, 3,3',4,4'-benzophenone tetracarboxylic acid.

Specific examples of acylphosphine oxides used as photopolymerization initiators include 2,4,6-trimethylbenzoyl diphenylphosphine oxide, 2,6-dimethoxybenzoyl diphenylphosphine oxide, 2,6-dichlorobenzoyl diphenylphosphine oxide, 2,4,6-trimethylbenzoyl methoxyphenylphosphine oxide, 2,4,6-trimethylbenzoyl ethoxyphenylphosphine oxide, 2,3,5,6-tetramethylbenzoyl diphenylphosphine oxide and benzoyldi-(2,6)-dimethylphenyl) phosphonate. Examples of bisacylphosphine oxides include bis-(2,6-dichlorobenzoyl) phenylphosphine oxide, bis-(2,6-dichlorobenzoyl)-2,5-dimethylphenyl phosphine oxide, bis-(2,6-dichlorobenzoyl)-4-propylphenyl phosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentyl phosphine oxide, bis-(2,6-dimethoxybenzoyl)-2,5-dimethylphenyl phosphine oxide, bis-(2,4,6-trimethylbenzoyl) phenylphosphine oxide and (2,5,6-trimethylbenzoyl)-2,4,4-trimethylpentylphosphine oxide.

Specific examples of thioxanthones or quaternary ammonium salts of thioxanthones used as photopolymerization initiators include thioxanthone, 2-chlorothioxanthene-9-one, 2-hydroxy-3-(9-oxy)-9H-thioxanthene-4-yloxy)-N,N,N-trimethyl-propaneaminium chloride, 2-hydroxy-3-(1-methyl-9-oxy-9H-thioxanthene-4-yloxy)-N,N,N-trimethyl-propaneaminium chloride, 2-hydroxy-3-(9-oxo-9H-thioxanthene-2-yloxy)-N,N,N-trimethyl-propaneaminium chloride, 2-hydroxy-3-(3,4-dimethyl-9-oxo-9H-thioxanthene-2-yloxy)-N,N,N-trimethyl-1-propane aminium chloride, 2-hydroxy-3-(3,4-dimethyl)-9H-thioxanthene-2-yloxy)-N, N, N-trimethyl-1-propaneaminium chloride, 2-hydroxy-3-(1,3,4-trimethyl-9-oxo-9H-thioxanthene-2yloxy)-N,N,N-trimethyl-1-propaneaminium chloride and the like.

Specific examples of α-diketones used as photopolymerization initiators include diacetyl, dibenzyl, camphorquinone, 1-phenyl-propane-1,2-dione, 2,3-pentadione, 2,3-octadione, 9,10-phenanthrenequinone (9,10-Phenanthrenequinone), 4,4'-oxybenzyl, acenaphthenequinone and the like.

Specific examples of coumarin compounds used as photopolymerization initiator include 3,3'-carbonyl bis (7-diethylamino coumarin), 3-(4-methoxybenzoyl) coumarin, 3-tyenoyl coumarin, 3-benzoyl-5,7-dimethoxy coumarin, 3-benzoyl-7-methoxy coumarin, 3-benzoyl-6-methoxy coumarin, 3-benzoyl-8-methoxy coumarin, 3-benzoyl coumarin, 7-methoxy-3-(p-nitrobenzoyl) coumarin, 3-(p-nitrobenzoyl) coumarin, 3-benzoyl-8-methoxy coumarin, 3,5-carbonyl bis (7-methoxy coumarin), 3-benzoyl-6-bromo coumarin, 3,3'-carbonyl bis coumarin, 3-benzoyl-7-dimethylamino coumarin, 3-benzoylbenzo [f] coumarin, 3-carboxy coumarin, 3-carboxy-7-methoxy coumarin, 3-ethoxycarbonyl-6-methoxy coumarin, 3-ethoxycarbonyl-8-methoxy coumarin, 3-acetylbenzo [f] coumarin, 7-methoxy-3-(p-nitrobenzoyl) coumarin, 3-(p-nitrobenzoyl) coumarin, 3-benzoyl-8-methoxy coumarin, 3-benzoyl-6-nitro coumarin, 3-benzoyl-7-diethylamino coumarin, 7-dimethylamino-3-(4-methoxybenzoyl) coumarin, 7-diethylamino-3-(4-methoxybenzoyl) coumarin, 7-diethylamino-3-(4-diethylamino) coumarin, 7-methoxy-3-(4-methoxybenzoyl) coumarin, 3-(4-nitrobenzoyl) benzo [f] coumarin, 3-(4-ethoxy cinnamoyl)-7-methoxy coumarin, 3-(4-dimethylamino cinnamoyl) coumarin, 3-(4-diphenylamino cinnamoyl) coumarin, 3-[(3-dimethylbenzo thiazole-2-ylidene) acetyl] coumarin, 3-[(1-methylnaphtho [1,2-d] thiazole-2-ylidene) acetyl] coumarin, 3,3'-carbonyl bis (6-methoxy coumarin), 3,3'-carbonyl bis (7-acetoxy coumarin), 3,3'-carbonyl bis (7-dimethylamino coumarin), 3-(2-benzothiazoyl)-7-(diethylamino) coumarin, 3-(2-benzothiazoyl)-7-(dibutylamino) coumarin, 3-(2-benzoimidazole)-7-(diethylamino) coumarin, 3-(2-benzothiazoyl)-7-(dioctylamino) coumarin, 3-acetyl-7-(dimethylamino) coumarin, 3,3'-carbonyl bis (7-dibutylamino coumarin), 3,3'-carbonyl-7-diethylamino coumarin, 7'-bis (butoxyethyl) amino coumarin, 10-[3-4-(dimethylamino) phenyl]-1-oxo-2-propenyl]-2,3,6,7-1,1,7,7-tetramethyl 1H, 5H, 11H-[1] benpyrano [6,7,8-ij] quinolizin-11-one, 10-(2-benzothiazoyl)-2,3,6,7-tetrahydro-1,1,7,7-tetramethyl 1H, 5H, 11H-[1] benzopyrano [6,7,8-ij] quinolizin-11-one.

Among the coumarin compounds, 3,3'-carbonyl bis (7-diethylamino coumarin) and 3,3'-carbonyl bis (7-dibutylamino coumarin) are particularly preferable.

Specific examples of anthraquinones used as photopolymerization initiators include anthraquinone, 1-chloro anthraquinone, 2-chloro anthraquinone, 1-bromo anthraquinone, 1,2-benz anthraquinone, 1-methyl anthraquinone, 2-ethyl anthraquinone and 1-hydroxy anthraquinone.

Specific examples of benzoin alkyl ethers used as photopolymerization initiators include benzoin methyl ether, benzoin ethyl ether, benzoin isopropyl ether and benzoin isobutyl ether.

Specific examples of α-aminoketones used as photopolymerization initiators include 2-methyl-[4-(methylthio) phenyl]-2-morpholinopropane-1-one.

As the (c) photopolymerization initiator, benzophenones, benzoins, acylphosphine oxides, α-diketones and derivatives thereof are preferable, acylphosphine oxides, α-diketones and derivatives thereof are particularly preferable, the examples include diphenyl (2,4,6-trimethylbenzoyl) phosphine oxide, 9,10-phenanthrenequinone, 1-phenyl-propane-1,2-dione and diacetyl.

By using these photopolymerization initiators, a composition for optical three-dimensional modeling exhibiting sufficient photocurability can be obtained.

These may be used alone or in combination of two or more.

The addition amount of the (c) photopolymerization initiator is preferably 0.1 to 5 pts.wt. based on 100 pts.wt. of the (a) (meth)acrylate-based polymerizable monomer, and more preferably 0.5 to 4 pts.wt., further preferably 0.8 to 3.5 pts.wt. When the addition amount of the (C) photopolymerization initiator is too large, there may be a problem that excess curing during modeling increases and discoloration occurs.

In the present invention, it is preferable that no polymerization initiator other than (c) photopolymerization initiator is contained.

Further, it is desirable that the photopolymerizable composition obtained by these blends has no thixotropic property and has a viscosity of 0.5 to 20 Pa·s measured at 23° C.

If the thixotropy is exhibited or the viscosity is too high, it is difficult to model by a 3D printer, and defects are likely to occur in the modeled object. On the other hand, when the viscosity is low, precipitation of fillers and pigments easily occur to cause color unevenness of the molded object.

In the photopolymerizable composition adjusted to have an appropriate viscosity, the (meth)acrylate and the cohesive inorganic filler interact well without separation. Therefore, the surface of the modeled object becomes having good appearance.

Further, known additives may be added to the photopolymerizable composition of the present invention to adjust color tone or paste properties. Examples of these additives include pigments and dyes as colorants, organic solvents, thickeners, ultraviolet absorbers, polymerization inhibitors, fluorescent agents and the like, and 0.0001 to 10 pts.wt. thereof can be added. In particular, it is preferable to include 0.0001 to 2 pts.wt. of additives such as a coloring material, an ultraviolet absorber, a fluorescent agent and the like, based on the total weight of the composition.

In the present invention, it is preferable that other additives other than pigments, dyes, organic solvents, thickeners, ultraviolet absorbers, polymerization inhibitors and fluorescent agents.

EXAMPLES

The present invention is described specifically with reference to Examples. However, the present invention is not limited to Examples.

<(a1) (meth)acrylate-based polymerizable monomer containing a urethane structure>
- (a1-1): 2,2,4-trimethyl hexamethylene bis (2-carbamoyloxyethyl) dimethacrylate
- (a1-2): 2,7,7,9,15-pentamethyl-4,13-dioxo-3,14-dioxa-5,12-diaza hexadecane-1,16-diyldiacrylate <(a2) (meth)acrylate-based polymerizable monomer not containing a urethane structure
- (a2-1): 2,2-bis (4-methacryloxy polyethoxyphenyl) propane
- (a2-2): triethylene glycol dimethacrylate <(a3) polyfunctional (meth) acrylate-based polymerizable monomer having a branched structure and at least 3 or more (meth)acrylate moieties>
- (a3-1): dipentaerythritol hexaacrylate (not containing urethane structure, the number of (meth) acrylate moieties=6)
- (a3-2): ditrimethylolpropane tetraacrylate (not containing urethane structure, the number of (meth) acrylate moieties=4)
- (a3-3): pentaerythritol triacrylate (not containing urethane structure, the number of (meth) acrylate moieties=3)

[(b) Cohesive Inorganic Filler]
- (b1): $SiO_2$: 85 wt. %, $ZrO_2$: 15 wt. %, frequency average particle diameter: 2 μm, specific surface area: 200 $m^2/g$
- (b2): $SiO_2$: 100 wt. %, frequency average particle diameter: 1 μm, specific surface area: 300 $m^2/g$
- (b3): $SiO_2$: 60 wt. %, $ZrO_2$: 40 wt. %, frequency average particle diameter: 15 μm, specific surface area: 10 $m^2/g$
- (b4): $SiO_2$: 50 wt. %, $ZrO_2$: 50 wt. %, frequency average particle diameter: 20 μm, specific surface area: 5 $m^2/g$

[(c) Photopolymerization Initiator]
- (c1): diphenyl (2,4,6-trimethylbenzoyl) phosphine oxide
- (c2): 2,6-dimethoxybenzoyl diphenylphosphine oxide

[Non-Cohesive Inorganic Filler]
$SiO_2/ZrO_{2=100/0}$, frequency average particle diameter: 0.5 μm, specific surface area: 8 $m^2/g$ Mixtures prepared by mixing (a1), (a2), and (a3) at the weight ratios described in the examples, adding (c) and mixing at 40° C. for 24 hours in a dark room were used as the mixture of the (a) and the (c).

The (b) cohesive inorganic filler was a surface-treated cohesive inorganic filler prepared by aggregating non-aggregated inorganic filler (frequency average particle diameter of primary particles: 30 nm), surface treating the surface of the aggregated filler with a surface treatment agent (γ-methacryloyloxy propyltrimethoxysilane) and drying.

[Method of Measuring Surface Area and Frequency Average Particle Diameter]

The surface area was measured by a specific surface area meter QUASRASORB (manufactured by Quantachrome Instruments). Further, the frequency average particle diameter was measured by a laser diffraction particle diameter analyzer (Microtrac SPA: manufactured by Nikkiso Co., Ltd.), and the 50% diameter was defined as the frequency average particle diameter.

[Preparation of Dental Photopolymerizable Composition for 3D Printers]

According to the description in the table of Examples, predetermined amounts of the (a) (meth)acrylate-based polymerizable monomer, the (b) cohesive inorganic filler and the (c) photopolymerization initiator were added into a container and mixed by a rotation/revolution mixer ARV-310 (manufactured by Syncy Corporation) to prepare the photopolymerizable compositions.

[Viscosity Measurement Method]

Viscosity of the photopolymerizable composition was measured by using a rotary rheometer (Physica MCR301, manufactured by Anton Paar) under the conditions of Temperature: 23° C. and Rotation Speed: 20 Rpm.

[Test Specimen Modeling]

The photopolymerizable composition prepared in the above [Preparation of dental photopolymerizable composition for 3D printers] was modeled into the shape of various test specimens by dental 3D printer DWP-80S (manufactured by DG SHAPE). After modeling, the modeled object was washed with ethanol for 10 minutes and dried. After storing for 24 hours, post-polymerization was carried out for 10 minutes by using a photopolymerization apparatus Solidilite V (manufactured by SHOFU Inc.) to prepare various test specimens.

[Excessive Curing Evaluation Method (Surface Roughness)]

The plate-shaped test specimen having 14×14×t1.0 mm was modeled. The surface of the plate-shaped test specimen was visually observed, and it was confirmed whether white turbidity or surface roughness was caused by excessive curing.

Further, the L*a*b values in the white background and the black background were measured by a spectrocolorimeter (CM-3500d: Konica Minolta). YB/YW was calculated as a contrast ratio from the Y value (YW) of white background measurement and the Y value (YB) of black background measurement.

When white turbidity occurs, the contrast ratio approaches 1. When the contrast ratio was 0.9 or more, it was determined that excessive curing was remarkable.

Excessive curing (white turbidity) was evaluated by four-level evaluation by color measurement and visual inspection.
- 0: No excessive curing or surface roughness were observed
- 1: Slight excessive curing and surface roughness were recognized.
- 2: Excessive curing and surface roughness were partially observed, but the appearance was not deteriorated.
- 3: The entire surface was covered with white due to excessive curing (excessive curing was remarkable).

[Bending Strength/Elastic Modulus Evaluation Method]

Rod-shaped test specimen having 2×2×25 mm was modeled. After being immersed in water at 37 f 2° C. for 24 hours, a three-point bending test was conducted using a universal material testing machine (model 5967 manufactured by Instron Co., Ltd.) at a crosshead speed of 1.0 mm/min and at a distance between supporting points of 20 mm. Each sample was evaluated with 6 test specimens, and the average value was calculated.

Those having a bending strength of 100 MPa or more were determined to be good.

Further, the flexural modulus was measured from the inclination of stress-strain curve in measuring.

[Evaluation of Appearance]
- A: No Excessive curing and surface roughness were observed.

B: Slight excessive curing and surface roughness were recognized.
C: Excessive curing and surface roughness were partially observed, but the appearance was not deteriorated.
D: The entire surface was covered with white due to excessive curing (excessive curing was remarkable).

[Evaluation of Mechanical Characteristics]
A: Bending strength was 120 MPa or more.
B: Bending strength was 105 to less than 120 MPa.
C: Bending strength was 90 to less than 105 MPa.
D: Bending strength was less than 90 MPa.

[Evaluation of Modelability]
A: Viscosity was 4.4 Pa·s or less: Good modeling.
B: Viscosity was higher than 4.4 to 10 Pa·s or less: Viscosity was a little high, but there was no problem in modeling.
C: Viscosity was higher than 10 to 19 Pa·s or less: Viscosity was high, and modeling defects sometimes occurred.
D: Viscosity was higher than 19 Pa·s: Modeling defects easily occurred.

TABLE 1

|  |  |  | Example 1 | Example 2 | Example 3 | Example 4 | Example 5 |
|---|---|---|---|---|---|---|---|
| (a) | (a1) | (a1-1) 2,2,4-trimethyl hexamethylene bis (2-carbamoyloxyethyl) dimethacrylate | 70 | 70 | 51 | 51 | 75 |
|  |  | (a1-2) 2,7,7,9,15-pentamethyl-4,13-dioxo-3,14-dioxa-5,12-diaza hexadecane-1,16-diyldiacrylate |  |  |  |  |  |
|  | (a2) | (a2-1) 2,2-bis (4-methacryloxy polyethoxyphenyl) propane | 27 | 23 | 46 | 42 | 24 |
|  |  | (a2-2) triethylene glycol dimethacrylate |  |  |  |  |  |
|  | (a3) | (a3-1) dipentaerythritol hexaacrylate (corresponds to a2) | 3 | 7 | 3 | 7 |  |
|  |  | (a3-2) ditrimethylolpropane tetraacrylate (corresponds to a2) |  |  |  |  | 1 |
|  |  | (a3-3) pentaerythritol triacrylate (corresponds to a2) |  |  |  |  |  |
|  |  | The number of (meth) acrylate moieties in branched structure | 6 | 6 | 6 | 6 | 4 |
| (a1) Total |  |  | 70 | 70 | 51 | 51 | 75 |
| (a2) Total |  |  | 30 | 30 | 49 | 49 | 25 |
| (a3) Total |  |  | 3 | 7 | 3 | 7 | 1 |
| (a) Total |  |  | 100 | 100 | 100 | 100 | 100 |
| (b) | (b1) SiO2: 85 wt. %, ZrO2: 15 wt. %, frequency average particle diameter: 2 μm, specific surface area: 200 m$^2$/g |  | 15 | 30 | 15 | 30 | 10 |
|  | (b2) SiO2: 100 wt. %, frequency average particle diameter: 1 μm, specific surface area: 300 m$^2$/g |  |  |  |  |  |  |
|  | (b3) SiO2: 60 wt. %, ZrO2: 40 wt. %, frequency average particle diameter: 15 μm, specific surface area: 10 m$^2$/g |  |  |  |  |  |  |
|  | (b4) SiO2: 50 wt. %, ZrO2: 50 wt. %, frequency average particle diameter: 20 μm, specific surface area: 5 m$^2$/g |  |  |  |  |  |  |
| (b) Total |  |  | 15 | 30 | 15 | 30 | 10 |
| (c) | (c1) diphenyl (2,4,6-trimethylbenzoyl) phosphine oxide |  | 0.8 | 3.5 | 0.8 | 3.5 | 0.5 |
|  | (c2) 2,6-dimethoxybenzoyl diphenylphosphine oxide |  |  |  |  |  |  |
| (c) Total |  |  | 0.8 | 3.5 | 0.8 | 3.5 | 0.5 |
| Non-cohesive inorganic filler(SiO2/ZrO2 = 100/0, frequency average particle diameter: 0.5 μm, specific surface area: 8 m$^2$/g) |  |  |  |  |  |  |  |
| Composition Total |  |  | 115.8 | 133.5 | 115.8 | 133.5 | 110.5 |
| Evaluation Result | Viscosity (Pa · s) |  | 2.2 | 4.0 | 1.9 | 3.8 | 2.1 |
|  | Excessive curing |  | 0 | 0 | 0 | 0 | 0 |
|  | Bending strength (Mpa) |  | 125 | 138 | 124 | 135 | 118 |
|  | Elastic modulus (Gpa) |  | 2.8 | 3.9 | 3.0 | 4.1 | 2.7 |
| Evaluation | Appearance |  | A | A | A | A | A |
|  | Mechanical characteristics |  | A | A | A | A | B |
|  | Modelability |  | A | A | A | A | A |

|  |  |  | Example 6 | Example 7 | Example 8 | Example 9 |
|---|---|---|---|---|---|---|
| (a) | (a1) | (a1-1) 2,2,4-trimethyl hexamethylene bis (2-carbamoyloxyethyl) dimethacrylate | 75 | 80 | 70 | 70 |
|  |  | (a1-2) 2,7,7,9,15-pentamethyl-4,13-dioxo-3,14-dioxa-5,12-diaza hexadecane-1,16-diyldiacrylate |  |  |  |  |
|  | (a2) | (a2-1) 2,2-bis (4-methacryloxy polyethoxyphenyl) propane | 15 | 5 | 30 | 13 |
|  |  | (a2-2) triethylene glycol dimethacrylate |  |  |  |  |
|  | (a3) | (a3-1) dipentaerythritol hexaacrylate (corresponds to a2) |  |  |  | 17 |
|  |  | (a3-2) ditrimethylolpropane tetraacrylate (corresponds to a2) | 10 |  |  |  |
|  |  | (a3-3) pentaerythritol triacrylate (corresponds to a2) |  | 15 |  |  |
|  |  | The number of (meth) acrylate moieties in branched structure | 4 | 3 |  | 6 |
| (a1) Total |  |  | 75 | 80 | 70 | 70 |
| (a2) Total |  |  | 25 | 20 | 30 | 30 |
| (a3) Total |  |  | 10 | 15 | 0 | 17 |
| (a) Total |  |  | 100 | 100 | 100 | 100 |
| (b) | (b1) SiO2: 85 wt. %, ZrO2: 15 wt. %, frequency average particle diameter: 2 μm, specific surface area: 200 m$^2$/g |  | 35 | 50 | 30 | 30 |
|  | (b2) SiO2: 100 wt. %, frequency average particle diameter: 1 μm, specific surface area: 300 m$^2$/g |  |  |  |  |  |

TABLE 1-continued

|  |  |  |  |  |  |
|---|---|---|---|---|---|
|  | (b3) SiO2: 60 wt. %, ZrO2: 40 wt. %, frequency average particle diameter: 15 μm, specific surface area: 10 m²/g | | | | |
|  | (b4) SiO2: 50 wt. %, ZrO2: 50 wt. %, frequency average particle diameter: 20 μm, specific surface area: 5 m²/g | | | | |
| (b) Total | | 35 | 50 | 30 | 30 |
| (c) | (c1) diphenyl (2,4,6-trimethylbenzoyl) phosphine oxide | 4 | 5 | 3.5 | 2 |
|  | (c2) 2,6-dimethoxybenzoyl diphenylphosphine oxide | | | | |
| (c) Total | | 4 | 5 | 3.5 | 2 |
| Non-cohesive inorganic filler(SiO2/ZrO2 = 100/0, frequency average particle diameter: 0.5 μm, specific surface area: 8 m²/g) | | | | | |
| Composition Total | | 139 | 155 | 133.5 | 132 |
| Evaluation Result | Viscosity (Pa · s) | 3.8 | 14 | 3.7 | 5.8 |
|  | Excessive curing | 0 | 2 | 2 | 0 |
|  | Bending strength (Mpa) | 115 | 134 | 134 | 108 |
|  | Elastic modulus (Gpa) | 4.2 | 4.4 | 3.7 | 5.1 |
| Evaluation | Appearance | A | B | B | A |
|  | Mechanical characteristics | B | A | A | B |
|  | Modelability | A | C | A | B |

TABLE 2

|  |  |  | Example 10 | Example 11 | Example 12 | Example 13 |
|---|---|---|---|---|---|---|
| (a) | (a1) | (a1-1) 2,2,4-trimethyl hexamethylene bis (2-carbamoyloxyethyl) dimethacrylate | 70 | 70 |  | 70 |
|  |  | (a1-2) 2,7,7,9,15-pentamethyl-4,13-dioxo-3,14-dioxa-5,12-diaza hexadecane-1,16-diyldiacrylate |  |  | 70 |  |
|  | (a2) | (a2-1) 2,2-bis (4-methacryloxy polyethoxyphenyl) propane | 23 | 23 | 23 |  |
|  |  | (a2-2) triethylene glycol dimethacrylate |  |  |  | 23 |
|  | (a3) | (a3-1) dipentaerythritol hexaacrylate (corresponds to a2) | 7 | 7 | 7 | 7 |
|  |  | (a3-2) ditrimethylolpropane tetraacrylate (corresponds to a2) |  |  |  |  |
|  |  | (a3-3) pentaerythritol triacrylate (corresponds to a2) |  |  |  |  |
|  |  | The number of (meth) acrylate moieties in branched structure | 6 | 6 | 6 | 6 |
| (a1) Total | | | 70 | 70 | 70 | 70 |
| (a2) Total | | | 30 | 30 | 30 | 30 |
| (a3) Total | | | 7 | 7 | 7 | 7 |
| (a) Total | | | 100 | 100 | 100 | 100 |
| (b) | (b1) SiO2: 85 wt. %, ZrO2: 15 wt. %, frequency average particle diameter: 2 μm, specific surface area: 200 m²/g | | 100 | 42 | 30 | 30 |
|  | (b2) SiO2: 100 wt. %, frequency average particle diameter: 1 μm, specific surface area: 300 m²/g | | | | | |
|  | (b3) SiO2: 60 wt. %, ZrO2: 40 wt. %, frequency average particle diameter: 15 μm, specific surface area: 10 m²/g | | | | | |
|  | (b4) SiO2: 50 wt. %, ZrO2: 50 wt. %, frequency average particle diameter: 20 μm, specific surface area: 5 m²/g | | | | | |
| (b) Total | | | 100 | 42 | 30 | 30 |
| (c) | (c1) diphenyl (2,4,6-trimethylbenzoyl) phosphine oxide | | 3.5 | 3.5 | 3.5 | 3.5 |
|  | (c2) 2,6-dimethoxybenzoyl diphenylphosphine oxide | | | | | |
| (c) Total | | | 3.5 | 3.5 | 3.5 | 3.5 |
| Non-cohesive inorganic filler(SiO2/ZrO2 = 100/0, frequency average particle diameter: 0.5 μm, specific surface area: 8 m²/g) | | | | | | |
| Composition Total | | | 203.5 | 145.5 | 133.5 | 133.5 |
| Evaluation Result | Viscosity (Pa · s) | | 11.0 | 4.2 | 3.9 | 4.1 |
|  | Excessive curing | | 2 | 0 | 0 | 0 |
|  | Bending strength (Mpa) | | 138 | 139 | 137 | 138 |
|  | Elastic modulus (Gpa) | | 3.9 | 3.9 | 3.8 | 3.8 |
| Evaluation | Appearance | | B | A | A | A |
|  | Mechanical characteristics | | A | A | A | A |
|  | Modelability | | C | A | A | A |

|  |  |  | Example 14 | Example 15 | Example 16 | Example 17 |
|---|---|---|---|---|---|---|
| (a) | (a1) | (a1-1) 2,2,4-trimethyl hexamethylene bis (2-carbamoyloxyethyl) dimethacrylate | 70 | 70 | 70 | 70 |
|  |  | (a1-2) 2,7,7,9,15-pentamethyl-4,13-dioxo-3,14-dioxa-5,12-diaza hexadecane-1,16-diyldiacrylate |  |  |  |  |
|  | (a2) | (a2-1) 2,2-bis (4-methacryloxy polyethoxyphenyl) propane | 23 | 23 | 23 | 23 |
|  |  | (a2-2) triethylene glycol dimethacrylate |  |  |  |  |
|  | (a3) | (a3-1) dipentaerythritol hexaacrylate (corresponds to a2) | 7 | 7 | 7 | 7 |

TABLE 2-continued

|  |  |  |  |  |  |
|---|---|---|---|---|---|
| | (a3-2) ditrimethylolpropane tetraacrylate (corresponds to a2) | | | | |
| | (a3-3) pentaerythritol triacrylate (corresponds to a2) | | | | |
| | The number of (meth) acrylate moieties in branched structure | 6 | 6 | 6 | 6 |
| (a1) Total | | 70 | 70 | 70 | 70 |
| (a2) Total | | 30 | 30 | 30 | 30 |
| (a3) Total | | 7 | 7 | 7 | 7 |
| (a) Total | | 100 | 100 | 100 | 100 |
| (b) | (b1) SiO2: 85 wt. %, ZrO2: 15 wt. %, frequency average particle diameter: 2 μm, specific surface area: 200 m²/g | | | | 30 |
| | (b2) SiO2: 100 wt. %, frequency average particle diameter: 1 μm, specific surface area: 300 m²/g | 30 | | | |
| | (b3) SiO2: 60 wt. %, ZrO2: 40 wt. %, frequency average particle diameter: 15 μm, specific surface area: 10 m²/g | | 30 | | |
| | (b4) SiO2: 50 wt. %, ZrO2: 50 wt. %, frequency average particle diameter: 20 μm, specific surface area: 5 m²/g | | | 30 | |
| (b) Total | | 30 | 30 | 30 | 30 |
| (c) | (c1) diphenyl (2,4,6-trimethylbenzoyl) phosphine oxide | 3.5 | 3.5 | 3.5 | |
| | (c2) 2,6-dimethoxybenzoyl diphenylphosphine oxide | | | | 3.5 |
| (c) Total | | 3.5 | 3.5 | 3.5 | 3.5 |
| Non-cohesive inorganic filler(SiO2/ZrO2 = 100/0, frequency average particle diameter: 0.5 μm, specific surface area: 8 m²/g) | | | | | |
| Composition Total | | 133.5 | 133.5 | 133.5 | 133.5 |
| Evaluation Result | Viscosity (Pa · s) | 4.6 | 3.0 | 2.4 | 3.9 |
| | Excessive curing | 0 | 0 | 0 | 0 |
| | Bending strength (Mpa) | 138 | 118 | 106 | 137 |
| | Elastic modulus (Gpa) | 3.9 | 3.9 | 3.9 | 3.9 |
| Evaluation | Appearance | A | A | A | A |
| | Mechanical characteristics | A | B | B | A |
| | Modelability | B | A | A | A |

[Details of Various Compositions]

In Examples 1 to 4, 8 to 9, 11 to 13 and 17 in the table, there was no excessive curing and a good appearance was observed. Further, the bending strength also indicated a value of 100 MPa or more, and it was confirmed that the strength characteristics were excellent.

In Example 5 in the table, since the amount of the (b) cohesive inorganic filler was small as compared with Examples 1 to 4, 8 to 9, 11 to 13 and 17, the elastic modulus was decreased and the bending strength was slightly decreased. However, it was confirmed that good physical properties were exhibited as a whole.

In Example 6 in the table, since the amount of the (a3) polyfunctional (meth) acrylate-based polymerizable monomer having a branched structure and at least 3 or more (meth)acrylate moieties in the (a) (meth)acrylate-based polymerizable monomer was large as compared with Examples 1 to 4, 8 to 9, 11 to 13 and 17, the bending strength was slightly decreased, however, it was confirmed that good physical properties were exhibited as a whole.

In Example 7 in the table, since the amount of the (b) cohesive inorganic filler was large as compared with Examples 1 to 4, 8 to 9, 11 to 13 and 17, the viscosity increased and excessive curing and surface roughness were observed, however, it was confirmed that good physical properties were exhibited as a whole.

In Example 8 in the table, the (a) (meth)acrylate-based polymerizable monomer does not contain (a3) polyfunctional (meth) acrylate-based polymerizable monomer having a branched structure and at least 3 or more (meth)acrylate moieties. Although surface roughness was observed, the appearance was not deteriorated and it was confirmed that good physical properties were exhibited as a whole.

In Example 9 in the table, the amount of the (a3) polyfunctional (meth) acrylate-based polymerizable monomer having a branched structure and at least 3 or more (meth)acrylate moieties in the (a) (meth)acrylate-based polymerizable monomer was large as compared with Examples 1 to 4, 8 to 9, 11 to 13 and 17. Although the viscosity increased and the flexural strength decreased, it was confirmed that good physical properties were exhibited as a whole.

In Example 10 in the table, the ratios of the (a) (meth) acrylate-based polymerizable monomer and the (b) cohesive inorganic filler were equal. Although the viscosity increased and deteriorations of the modelability and appearance were observed, it was confirmed that good physical properties were exhibited as a whole.

In Example 14 in the table, since the particle size of the (b) cohesive inorganic filler was small and the specific surface area of the (b) cohesive inorganic filler was large as compared with Examples 1 to 4, 8 to 9, 11 to 13 and 17, the viscosity was increased and the modelability deteriorated, however, it was confirmed that good physical properties were exhibited as a whole.

In Examples 15 and 16 in the table, since the particle size of the (b) cohesive inorganic filler was large and the specific surface area of the (b) cohesive inorganic filler was small as compared with Examples 1 to 4, 8 to 9, 11 to 13 and 17, the viscosity was decrease to become brittle and the bending strength was lowered, however, it was confirmed that good physical properties were exhibited as a whole.

TABLE 3

|  |  |  | Comparative Example 1 | Comparative Example 2 | Comparative Example 3 | Comparative Example 4 | Comparative Example 5 |
|---|---|---|---|---|---|---|---|
| (a) | (a1) | (a1-1) 2,2,4-trimethyl hexamethylene bis (2-carbamoyloxyethyl) dimethacrylate | 70 | 70 | 40 | 70 | 85 |
|  |  | (a1-2) 2,7,7,9,15-pentamethyl-4,13-dioxo-3,14-dioxa-5,12-diaza hexadecane-1,16-diyldiacrylate |  |  |  |  |  |
|  | (a2) | (a2-1) 2,2-bis (4-methacryloxy polyethoxyphenyl) propane | 27 | 23 | 57 | 27 | 8 |
|  |  | (a2-2) triethylene glycol dimethacrylate |  |  |  |  |  |
|  | (a3) | (a3-1) dipentaerythritol hexaacrylate (corresponds to a2) | 3 | 7 | 3 | 3 | 7 |
|  |  | (a3-2) ditrimethylolpropane tetraacrylate (corresponds to a2) |  |  |  |  |  |
|  |  | (a3-3) pentaerythritol triacrylate (corresponds to a2) |  |  |  |  |  |
|  |  | The number of (meth) acrylate moieties in branched structure | 6 | 6 | 6 | 6 | 0 |
| (a1) Total |  |  | 70 | 70 | 40 | 70 | 85 |
| (a2) Total |  |  | 30 | 30 | 60 | 30 | 15 |
| (a3) Total |  |  | 3 | 7 | 3 | 3 | 7 |
| (a) Total |  |  | 100 | 100 | 100 | 100 | 100 |
| (b) | (b1) SiO2: 85 wt. %, ZrO2: 15 wt. %, frequency average particle diameter: 2 μm, specific surface area: 200 m$^2$/g |  | 105 |  | 30 |  | 30 |
|  | (b2) SiO2: 100 wt. %, frequency average particle diameter: 1 μm, specific surface area: 300 m$^2$/g |  |  |  |  |  |  |
|  | (b3) SiO2: 60 wt. %, ZrO2: 40 wt. %, frequency average particle diameter: 15 μm, specific surface area: 10 m$^2$/g |  |  |  |  |  |  |
|  | (b4) SiO2: 50 wt. %, ZrO2: 50 wt. %, frequency average particle diameter: 20 μm, specific surface area: 5 m$^2$/g |  |  |  |  |  |  |
| (b) Total |  |  | 105 | 0 | 30 | 0 | 30 |
| (c) | (c1) diphenyl (2,4,6-trimethylbenzoyl) phosphine oxide |  | 0.8 | 3.5 | 3.5 | 0.8 | 3.5 |
|  | (c2) 2,6-dimethoxybenzoyl diphenylphosphine oxide |  |  |  |  |  |  |
| (c) Total |  |  | 0.8 | 3.5 | 3.5 | 0.8 | 3.5 |
| Non-cohesive inorganic filler(SiO2/ZrO2 = 100/0, frequency average particle diameter: 0.5 μm, specific surface area: 8 m$^2$/g) |  |  |  | 30 |  |  |  |
| Composition Total |  |  | 205.8 | 133.5 | 133.5 | 100.8 | 133.5 |
| Evaluation Result | Viscosity (Pa · s) |  | 21 | 3.7 | 3.1 | 1.9 | 4.5 |
|  | Excessive curing |  | 3 | 3 | 3 | 0 | 0 |
|  | Bending strength (Mpa) |  | 136 | 98 | 99 | 80 | 89 |
|  | Elastic modulus (Gpa) |  | 4.8 | 3.8 | 4.1 | 2.2 | 2.9 |
| Evaluation | Appearance |  | D | D | D | A | A |
|  | Mechanical characteristics |  | A | D | D | D | D |
|  | Modelability |  | D | A | A | A | B |

In Comparative Example 1, the (b) cohesive inorganic filler was excessively contained. The viscosity increased, and the entire surface of the modeled object was covered with white due to excessive curing.

In Comparative Example 2, a non-cohesive inorganic filler was contained. The entire surface of the modeled object was covered with white due to excessive curing. In addition, bending strength was low, and good physical properties could not be obtained as a whole.

In Comparative Example 3, a large amount of the (a2) (meth)acrylate-based polymerizable monomer not containing a urethane structure was contained in the (a) (meth)acrylate-based polymerizable monomer. The entire surface of the modeled object was covered with white due to excessive curing. Further, the bending strength indicated a low value, and good physical properties could not be obtained.

In Comparative Example 4, the (b) cohesive inorganic filler was not contained. The bending strength was low and good physical properties could not be obtained.

In Comparative Example 5, a large amount of the (a1) (meth)acrylate-based polymerizable monomer containing a urethane structure was contained in the (a) (meth)acrylate-based polymerizable monomer. Since the viscosity was high, the elastic modulus was lowered, the bending strength was lowered, and good physical properties could not be obtained.

In addition, it was confirmed that, similar results were obtained even when the components further contained 0.1 pts.wt. of the coloring material and the ultraviolet absorber in the examples of the present description.

With respect to the use of substantially any plural and/or singular terms herein, those having skill in the art can translate from the plural to the singular and/or from the singular to the plural as is appropriate to the context. Although the description herein has been given with reference to the drawings and embodiments, it should be noted that those skilled in the art may make various changes and modifications on the basis of this invention without difficulty. Accordingly, any such changes and modifications are intended to be included in the scope of the embodiments.

INDUSTRIAL APPLICABILITY

The present invention can be used in the industry of manufacturing dental restorations with 3D printers using photopolymerizable compositions.

What is claimed is:

1. A dental photopolymerizable composition for 3D printer comprising:
   a (a) (meth)acrylate-based polymerizable monomer consisting of a (a1) (meth)acrylate-based polymerizable monomer containing a urethane structure, a (a2) (meth) acrylate-based polymerizable monomer not containing a urethane structure, and optionally, a (a3) polyfunctional (meth) acrylate-based polymerizable monomer having a branched structure and at least 3 or more (meth)acrylate moieties, a (b) cohesive inorganic filler in which nano-sized primary particles are aggregated, and a (c) photopolymerization initiator, wherein;

a ratio of the (a1) (meth)acrylate-based polymerizable monomer containing a urethane structure and the (a2) (meth)acrylate-based polymerizable monomer not containing a urethane structure in the (a) (meth)acrylate-based polymerizable monomer is 51 to 80: 49 to 20 pts.wt., a ratio of the (a) (meth)acrylate-based polymerizable monomer and the (b) cohesive inorganic filler is 65 to 90: 35 to 10 pts.wt., the dental photopolymerizable composition for 3D printer contains 0.1 to 5 pts.wt. of the (c) photopolymerization initiator based on 100 pts.wt. of the (a) (meth)acrylate-based polymerizable monomer, and the (b) cohesive inorganic filler consists of 60 to 100 wt. % of $SiO_2$ and 0 to 40 wt. % of $ZrO_2$.

2. The dental photopolymerizable composition for 3D printer according to claim 1, wherein, the (a) (meth)acrylate-based polymerizable monomer has the (a3) polyfunctional (meth) acrylate-based polymerizable monomer having a branched structure and at least 3 or more (meth)acrylate moieties.

3. The dental photopolymerizable composition for 3D printer according to claim 1, wherein, the (a3) polyfunctional (meth) acrylate-based polymerizable monomer having a branched structure and at least 3 or more (meth)acrylate moieties consists of the (a2) (meth)acrylate-based polymerizable monomer not containing a urethane structure.

4. A dental photopolymerizable composition for 3D printer comprising:

a (a) (meth)acrylate-based polymerizable monomer consisting of a (a1) (meth)acrylate-based polymerizable monomer containing a urethane structure, a (a2) (meth) acrylate-based polymerizable monomer not containing a urethane structure, and optionally, a (a3) polyfunctional (meth) acrylate-based polymerizable monomer having a branched structure and at least 3 or more (meth)acrylate moieties, a (b) cohesive inorganic filler in which nano-sized primary particles are aggregated, and a (c) photopolymerization initiator, wherein;

a ratio of the (a1) (meth)acrylate-based polymerizable monomer containing a urethane structure and the (a2) (meth)acrylate-based polymerizable monomer not containing a urethane structure in the (a) (meth)acrylate-based polymerizable monomer is 51 to 80: 49 to 20 pts.wt., a ratio of the (a) (meth)acrylate-based polymerizable monomer and the (b) cohesive inorganic filler is 65 to 90: 35 to 10 pts.wt., and the specific surface area of the (b) cohesive inorganic filler is 10 to 300 $m^2/g$.

5. The dental photopolymerizable composition for 3D printer according to claim 1, wherein, the frequency average particle diameter of the (b) cohesive inorganic filler is within a range of 1 to 15 μm.

6. The dental photopolymerizable composition for 3D printer according to claim 1, wherein, the dental photopolymerizable composition for 3D printer further contains an additive.

7. The dental photopolymerizable composition for 3D printer according to claim 6, wherein, the additive contains one or more selected from the group consisting of a coloring material, an ultraviolet absorber, a polymerization inhibitor and a fluorescent agent.

8. The dental photopolymerizable composition for 3D printer according to claim 6, wherein, the dental photopolymerizable composition for 3D printer contains 0.0001 to 2 pts.wt. of the additive based on 100 pts.wt. of the dental photopolymerizable composition for 3D printer excluding the additive.

9. A dental restoration prepared by a stereolithography-type 3D printer by using the dental photopolymerizable composition for 3D printer according to claim 1.

10. The dental photopolymerizable composition for 3D printer according to claim 2, wherein, the (a3) polyfunctional (meth) acrylate-based polymerizable monomer having a branched structure and at least 3 or more (meth)acrylate moieties consists of the (a2) (meth)acrylate-based polymerizable monomer not containing a urethane structure.

11. The dental photopolymerizable composition for 3D printer according to claim 4, wherein, the (b) cohesive inorganic filler consists of 60 to 100 wt. % of $SiO_2$ and 0 to 40 wt. % of $ZrO_2$.

12. The dental photopolymerizable composition for 3D printer according to claim 1, wherein, the specific surface area of the (b) cohesive inorganic filler is 10 to 300 $m^2/g$.

13. The dental photopolymerizable composition for 3D printer according to claim 4, wherein, the frequency average particle diameter of the (b) cohesive inorganic filler is within a range of 1 to 15 μm.

14. The dental photopolymerizable composition for 3D printer according to claim 4, wherein, the dental photopolymerizable composition for 3D printer further contains an additive.

15. The dental photopolymerizable composition for 3D printer according to claim 4, wherein, the additive contains one or more selected from the group consisting of a coloring material, an ultraviolet absorber, a polymerization inhibitor and a fluorescent agent.

16. The dental photopolymerizable composition for 3D printer according to claim 4, wherein, the dental photopolymerizable composition for 3D printer contains 0.0001 to 2 pts.wt. of the additive based on 100 pts.wt. of the dental photopolymerizable composition for 3D printer excluding the additive.

17. A dental restoration prepared by a stereolithography-type 3D printer by using the dental photopolymerizable composition for 3D printer according to claim 16.

18. A dental photopolymerizable composition for 3D printer comprising:

a (a) (meth)acrylate-based polymerizable monomer consisting of a (a1) (meth)acrylate-based polymerizable monomer containing a urethane structure, a (a2) (meth) acrylate-based polymerizable monomer not containing a urethane structure, and optionally, a (a3) polyfunctional (meth) acrylate-based polymerizable monomer having a branched structure and at least 3 or more (meth)acrylate moieties, a (b) cohesive inorganic filler in which nano-sized primary particles are aggregated, and a (c) photopolymerization initiator, wherein;

a ratio of the (a1) (meth)acrylate-based polymerizable monomer containing a urethane structure and the (a2) (meth)acrylate-based polymerizable monomer not containing a urethane structure in the (a) (meth)acrylate-based polymerizable monomer is 51 to 80: 49 to 20 pts.wt., a ratio of the (a) (meth)acrylate-based polymerizable monomer and the (b) cohesive inorganic filler is 65 to 90: 35 to 10 pts.wt., the dental photopolymerizable composition for 3D printer contains 0.1 to 5 pts.wt. of the (c) photopolymerization initiator based on 100 pts.wt. of the (a) (meth)acrylate-based polymerizable monomer, and the dental photopolymerizable composition for 3D printer contains no other filler other than the (b) cohesive inorganic filler.

19. The dental photopolymerizable composition for 3D printer according to claim 18, wherein, the (a) (meth)acrylate-based polymerizable monomer has a (a3) polyfunctional (meth) acrylate-based polymerizable monomer having a branched structure and at least 3 or more (meth)acrylate moieties.

\* \* \* \* \*